(12) United States Patent
Balkovec

(10) Patent No.: US 12,420,067 B2
(45) Date of Patent: Sep. 23, 2025

(54) GUIDEWIRE ASSEMBLY

(71) Applicant: Boston Scientific Medical Device Limited, Ballybrit (IE)

(72) Inventor: Christian Balkovec, Kitchener (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 433 days.

(21) Appl. No.: 17/314,194

(22) Filed: May 7, 2021

(65) Prior Publication Data

US 2021/0353913 A1 Nov. 18, 2021

Related U.S. Application Data

(60) Provisional application No. 63/023,426, filed on May 12, 2020.

(51) Int. Cl.
*A61M 25/09* (2006.01)
*A61M 25/06* (2006.01)

(52) U.S. Cl.
CPC .... *A61M 25/09041* (2013.01); *A61M 25/065* (2013.01); *A61M 25/09* (2013.01); *A61M 2025/09141* (2013.01)

(58) Field of Classification Search
CPC .. A61M 2005/1585; A61M 2037/0023; A61M 25/09041; A61M 25/09; A61M 2025/09141
See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |

(Continued)

FOREIGN PATENT DOCUMENTS

WO WO-2019113043 A1 * 6/2019 ......... A61B 17/3468

*Primary Examiner* — William R Carpenter
(74) *Attorney, Agent, or Firm* — Nelson Mullins Riley & Scarborough LLP

(57) ABSTRACT

A guidewire assembly configured to be deployed from an ancillary assembly. The guidewire assembly has a distal puncture tip extending from a deployed distal-shaped section configured to mitigate piercing tip touch back on a biological wall after the elongated guidewire assembly is deployed from the ancillary assembly, and the distal puncture tip crosses a biological wall.

17 Claims, 8 Drawing Sheets

(56) References Cited

U.S. PATENT DOCUMENTS

| | | |
|---|---|---|
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B2 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |

(56) References Cited

U.S. PATENT DOCUMENTS

| | | |
|---|---|---|
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 10,368,911 B2 | 8/2019 | Davis et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1* | 3/2005 | Hartley ............... A61B 18/1492 606/41 |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105654 A1* | 4/2009 | Kurth ............... A61M 25/09041 604/170.03 |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2017/0266417 A1* | 9/2017 | Sundler ............... A61M 25/09 |
| 2019/0021763 A1 | 1/2019 | Zhou et al. |
| 2019/0247035 A1 | 8/2019 | Gittard et al. |

\* cited by examiner

//GUIDEWIRE ASSEMBLY

TECHNICAL FIELD

This document relates to the technical field of (and is not limited to) (A) an elongated guidewire assembly for use with an ancillary assembly, (B) a combination of an elongated guidewire assembly and an ancillary assembly, and (C) a method of using an ancillary assembly and an elongated guidewire assembly.

BACKGROUND

Known medical devices are configured to facilitate a medical procedure and help healthcare providers diagnose and/or treat medical conditions of sick patients.

SUMMARY

It will be appreciated that there exists a need to mitigate (at least in part) at least one problem associated with the existing (known) guidewires (also called the existing technology). After much study of, and experimentation with, the existing (known) guidewires, an understanding (at least in part) of the problem and its solution have been identified (at least in part) and are articulated (at least in part) as follows:

When deploying a J-shaped guidewire (via a dilator) with a piercing tip (or an electrically-activated distal tip) across the interatrial septum (of the heart of a patient), there may be a chance for the piercing tip of the guidewire to touch back on the septum (such as, when the operator has not sufficiently tented the septum with the dilator). This condition may create an additional (unwanted) puncture site and/or inadvertent tissue trauma, and both cases may not be desirable.

This may be particularly problematic with radiofrequency guidewires that rely on radio frequency energy emitted from the active tip to puncture the tissue (wall), where mere proximity and/or light physical contact with the tissue may result in inadvertent tissue vaporization (damage). Dilator tenting may be common in transseptal catheterization procedures, and refers to the deformation of the tissue when a relatively stiffer accessory device (such as the dilator) depresses the tissue and creates a tent shape (in the tissue wall) as the relatively stiffer accessory device is made to apply a localized force to the tissue. This case may enable the user to achieve good contact with a biological wall (such as the interatrial septum of the heart) and optimize the site that the guidewire may cross through. Creating a depression in the tissue (the tissue wall) on the right side of the tissue wall may result in an elevated tent of tissue on the left side of the tissue wall. Thus, when the known piercing guidewire is deployed through the accessory device, the tent of tissue provides the guidewire with enough elevation and clearance from the septum that the piercing tip (puncturing tip) does not touch back onto another portion of the tissue wall when returning to a relaxed "J" configuration of the guidewire. Occasionally, it may not be possible to achieve significant (or any) levels of dilator tenting, and this clearance for the J-type guidewire to deploy and return to a relaxed configuration without touching back (a touch back condition) onto the septum may not exist.

Referring to the embodiments as depicted in FIG. 1 to FIG. 5, there is depicted a known guidewire assembly. The known guidewire assembly may include the known J-type guidewire. The known guidewire assembly is configured to be deployed across the septum (a biological wall) of the heart. The design of the known guidewire assembly, unfortunately, exposes the biological wall of the patient to a touch back condition on the biological wall (such as the septum), particularly if there is insufficient tenting applied by an ancillary assembly (from which the known guidewire assembly may be deployed).

Referring to the embodiment as depicted in FIG. 1, the ancillary assembly is positioned adjacently to (or abut, contact, etc., and any equivalent thereof) the biological wall. The puncture tip (of the known guidewire assembly) is initially deployed (to extend) from the ancillary assembly (after the ancillary assembly is positioned adjacently to, or contact, the biological wall). The biological wall becomes initially punctured by movement of the puncture tip, thereby forming a puncture hole through the biological wall. Behind the puncture tip extends a first linear portion (a straight portion) of the known guidewire assembly.

Referring to the embodiment as depicted in FIG. 2, the puncture tip and the first linear portion are further extended (deployed) from the ancillary assembly. A first inflection portion is formed from an end of the first linear portion. The first inflection portion is a point at which a change in the direction of curvature occurs. A curved portion extends from the first inflection portion.

Referring to the embodiment as depicted in FIG. 3, the puncture tip and the first linear portion continue to become further extended (deployed) from the ancillary assembly; in this manner, a longer length of the curved portion becomes revealed or exposed from the interior of the ancillary assembly. The puncture tip bends (that is, bends to the right side of FIG. 3, by way of illustration) because of the degree of curvature exposed by the curved portion that becomes revealed with further deployment of the known guidewire assembly. As a result of further extension of the curved portion from the interior of the ancillary assembly, the puncture tip inadvertently formed a second puncture (at the potential puncture site) that extends through the biological wall. This is not a desirable condition (since the deployment of the curved portion is not yet completed). The curved portion is now partially formed (partially deployed), and the patient may be damaged which may require further surgical time to repair, etc.

Referring to the embodiment as depicted in FIG. 4, the puncture tip is further extended or deployed from the ancillary assembly. In this manner, a second inflection portion is revealed or exposed from the ancillary assembly. The second inflection portion is a point at which a change in the direction of curvature occurs. Once the second inflection portion is revealed, the curved portion becomes fully formed (fully deployed). The second linear portion extends behind the second inflection portion. Unfortunately, the puncture tip is forced to extend even further past to and beyond the biological wall, and cause more unwanted damage to the biological wall of the patient. The curved portion is configured or formed to reduce trauma when contacting a biological structure (as originally designed); however, unwanted damage has been inflicted at the puncture site.

Referring to the embodiment as depicted in FIG. 5, the puncture tip includes an energy emitting device (such as a radio frequency device) configured to puncture and form a hole through the biological wall (once activated accordingly). As depicted in FIG. 5, the puncture tip is not yet activated; however, the puncture tip is forced to form (temporarily) a tent in the biological wall. The forced formation of the tent is not desirable since the puncture tip may inadvertently puncture the biological wall even though the puncture tip is not yet activated (by sheer brute force movement of the puncture tip through the biological wall). This condition is not desirable.

In view of the foregoing, it may be desirable to provide an elongated guidewire assembly having a distal puncture tip configured to be received in an elongated lumen of the ancillary assembly. The elongated guidewire assembly is configured to form a deployed distal-shaped section (either after and/or while the elongated guidewire assembly is deployed from the exit portal). The distal puncture tip is (preferably) configured to puncture the first tissue portion of the biological wall and form a puncture hole extending through the first tissue portion. The distal puncture tip (preferably) is also configured to extend toward, and become positioned adjacently to, without puncturing, the second tissue portion of the biological wall of the patient.

To mitigate, at least in part, at least one problem associated with the existing technology, there is provided (in accordance with a major aspect) an apparatus. The apparatus is for (is configured to use with) an ancillary assembly. The apparatus includes and is not limited to (comprises) an elongated guidewire assembly configured to be deployed from the ancillary assembly. The guidewire assembly has a distal puncture tip extending from a deployed distal-shaped section configured to mitigate piercing-tip touching back (that is, mitigate or prevent the piercing tip from touching back) on a biological wall after the elongated guidewire assembly is deployed from the ancillary assembly, and the distal puncture tip crosses a biological wall.

To mitigate, at least in part, at least one problem associated with the existing technology, there is provided (in accordance with a major aspect) an apparatus. The apparatus is for (is configured to use with) an ancillary assembly having an exit portal configured to be positioned proximate to (to preferably abut or contact) a first tissue portion and a second tissue portion of a biological wall of a patient. The apparatus includes and is not limited to (comprises) an elongated guidewire assembly having a distal puncture tip configured to be received in an elongated lumen of the ancillary assembly. The elongated guidewire assembly and the distal puncture tip are configured to be deployed, at least in part, from the exit portal of the ancillary assembly; this is done (preferably) in such a way that the elongated guidewire assembly, in a deployed condition, forms a deployed distal-shaped section after the elongated guidewire assembly is deployed from the exit portal. The distal puncture tip (preferably) extends from (is configured to extend from) a distal portion of the deployed distal-shaped section. This is done, preferably, after the elongated guidewire assembly is deployed from the exit portal. The distal puncture tip is (preferably) also configured to puncture the first tissue portion of the biological wall and form a puncture hole extending through the first tissue portion of the biological wall; this is done (preferably) after (A) the exit portal is positioned proximate to (abuts or contacts) the first tissue portion of the biological wall, and (B) the distal puncture tip is deployed from the exit portal toward the second tissue portion of the biological wall. The distal puncture tip (preferably) is also configured to extend toward, and become positioned adjacently to, without puncturing, the second tissue portion of the biological wall of the patient; this is done (preferably) after (A) the exit portal, in use, abuts (contacts) the first tissue portion, and (B) the distal puncture tip is deployed from the exit portal, and the distal puncture tip, in use, forms the puncture hole extending through the biological wall.

To mitigate, at least in part, at least one problem associated with the existing technology, there is provided (in accordance with a major aspect) an apparatus. The apparatus includes and is not limited to (comprises) a synergistic combination of an ancillary assembly and an elongated guidewire assembly. The ancillary assembly (preferably) has an exit portal configured to be positioned proximate to (to preferably abut or contact) a first tissue portion and a second tissue portion of a biological wall of a patient. The elongated guidewire assembly has a distal puncture tip configured (preferably) to be received in an elongated lumen of the ancillary assembly. The elongated guidewire assembly and the distal puncture tip are (preferably) configured to be deployed, at least in part, from the exit portal of the ancillary assembly in such a way that the elongated guidewire assembly, in a deployed condition, forms a deployed distal-shaped section after the elongated guidewire assembly is deployed from the exit portal. The distal puncture tip (preferably) extends from a distal portion of the deployed distal-shaped section after the elongated guidewire assembly is deployed from the exit portal.

The distal puncture tip is (preferably) also configured to puncture the first tissue portion of the biological wall and form a puncture hole extending through the first tissue portion of the biological wall; this is done (preferably) after: (A) the exit portal is positioned proximate to (abuts or contacts) the first tissue portion of the biological wall, and (B) the distal puncture tip is deployed from the exit portal toward the second tissue portion of the biological wall. The distal puncture tip is also configured to extend toward, and become positioned adjacently to, without puncturing, the second tissue portion of the biological wall of the patient; this is done (preferably) after (A) the exit portal, in use, abuts (contacts) the first tissue portion, and (B) the distal puncture tip is deployed from the exit portal, and the distal puncture tip, in use, forms the puncture hole extending through the biological wall.

To mitigate, at least in part, at least one problem associated with the existing technology, there is provided (in accordance with a major aspect) a method. The method is for a manner of using an ancillary assembly and an elongated guidewire assembly. The ancillary assembly has an exit portal configured to be positioned proximate to (to preferably abut or contact) a first tissue portion and a second tissue portion of a biological wall of a patient. The elongated guidewire assembly has a distal puncture tip configured to be received in an elongated lumen of the ancillary assembly. The method includes deploying, at least in part, the elongated guidewire assembly and the distal puncture tip from the exit portal of the ancillary assembly in such a way that the elongated guidewire assembly, in a deployed condition, forms a deployed distal-shaped section after the elongated guidewire assembly is deployed from the exit portal. The method also includes extending the distal puncture tip from a distal portion of the deployed distal-shaped section after the elongated guidewire assembly is deployed from the exit portal. The method also includes puncturing, with the distal puncture tip, the first tissue portion of the biological wall and forming a puncture hole extending through the first tissue portion of the biological wall; this is done (preferably) after (A) the exit portal is positioned proximate to (abuts or contacts) the first tissue portion of the biological wall, and (B) the distal puncture tip is deployed from the exit portal toward the second tissue portion of the biological wall. The method also includes extending and positioning the distal puncture tip toward and adjacent to, without puncturing, the second tissue portion of the biological wall of the patient; this is done after (A) the exit portal, in use, abuts (contacts) the first tissue portion, and (B) the distal puncture tip is deployed from the exit portal, and the distal puncture tip, in use, forms the puncture hole extending through the biological wall.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
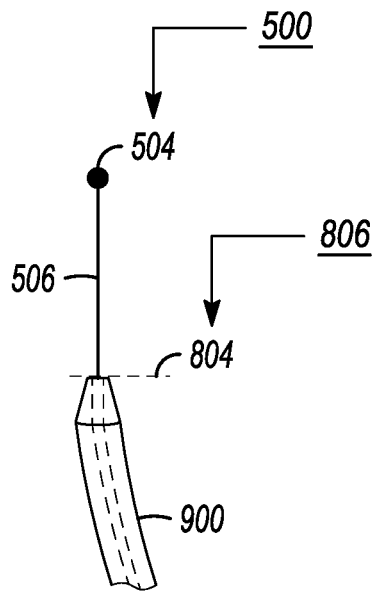
FIG. 1 depicts side view of a known guidewire assembly with the ancillary assembly positioned adjacently to the biological wall.
Figure 2:
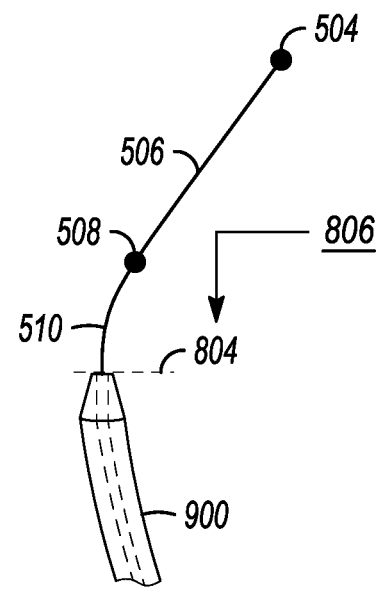
FIG. 2 depicts side view of a known guidewire assembly with the puncture tip and the first linear portion further extended from the ancillary assembly.
Figure 3:
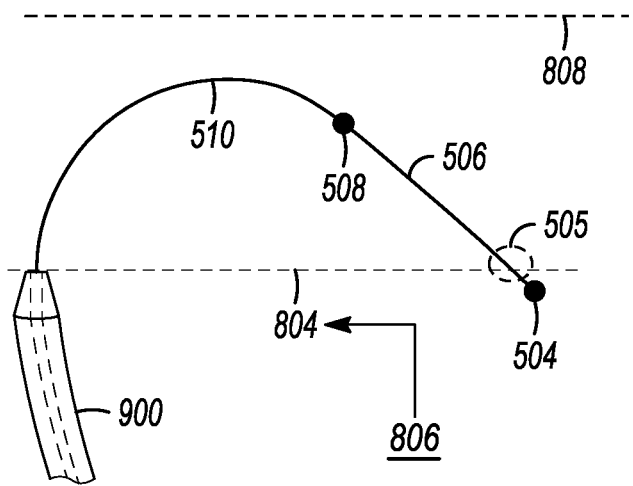
FIG. 3 depicts side view of a known guidewire assembly with the puncture tip and the first linear portion extended from the ancillary assembly.
Figure 4:
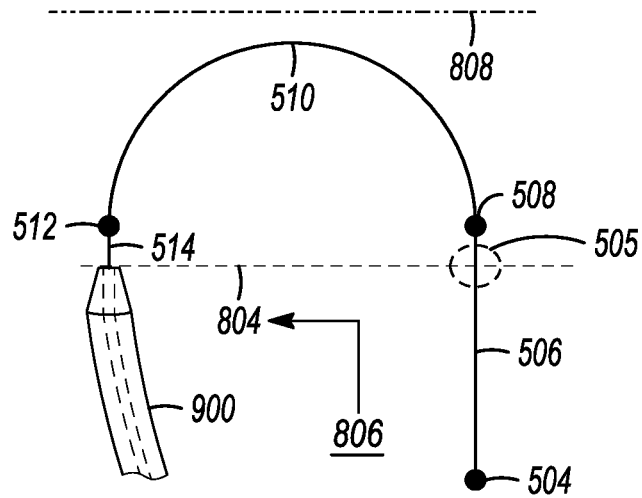
FIG. 4 depicts side view of a known guidewire assembly with the puncture tip further extended or deployed from the ancillary assembly.

The drawings are not necessarily to scale and may be illustrated by phantom lines, diagrammatic representations, and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are in commercially feasible embodiments are often not depicted to provide a less obstructed view of the embodiments of the present disclosure.

LISTING OF REFERENCE NUMERALS USED IN THE DRAWINGS guidewire assembly 100
electrical-insulation layer 101
deployed distal-shaped section 102
distal puncture tip 104
first linear portion 106
first inflection portion 108
intermediate portion 110
second inflection portion 112
second linear portion 114
relative offset 116
tip-to-wall distance 118
inflection portion-to-wall distance 120
deployment direction 200
known guidewire assembly 500
puncture tip 504
potential puncture site 505
first linear portion 506
first inflection portion 508
curved portion 510
second inflection portion 512
second linear portion 514
first tissue portion 801
second tissue portion 802
puncture hole 803
biological wall 804
patient 806
biological structure 808
ancillary assembly 900
lumen 901
exit portal 902

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary, or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

FIG. 6 to FIG. 11 depict side views of embodiments of an elongated guidewire assembly 100.

Figure 6:
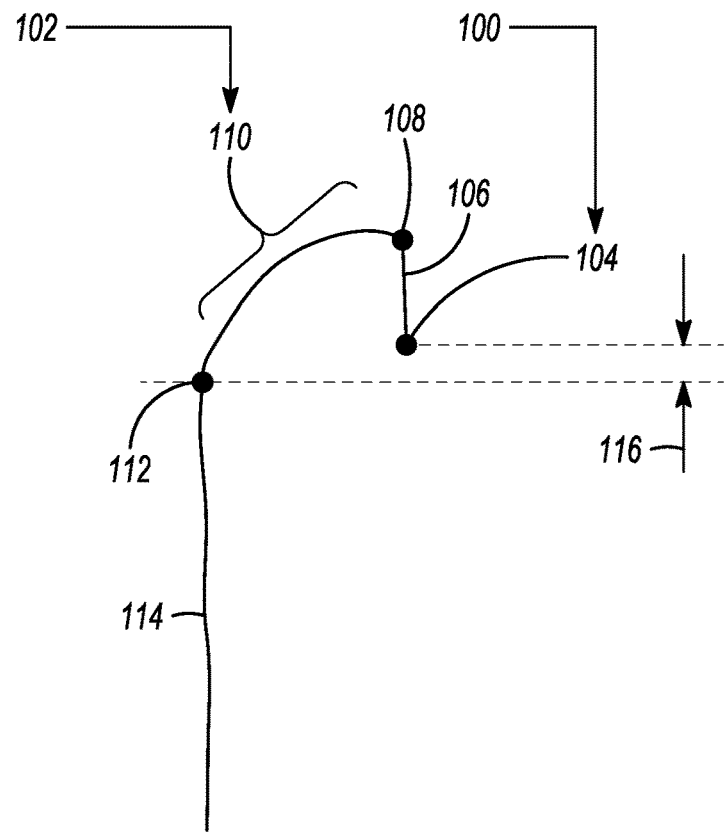
FIG. 6 to FIG. 11 depict side views of embodiments of an elongated guidewire assembly.

FIG. 12 to FIG. 17 depict side views of embodiments of the elongated guidewire assembly 100 of FIG. 6.

Figure 10:
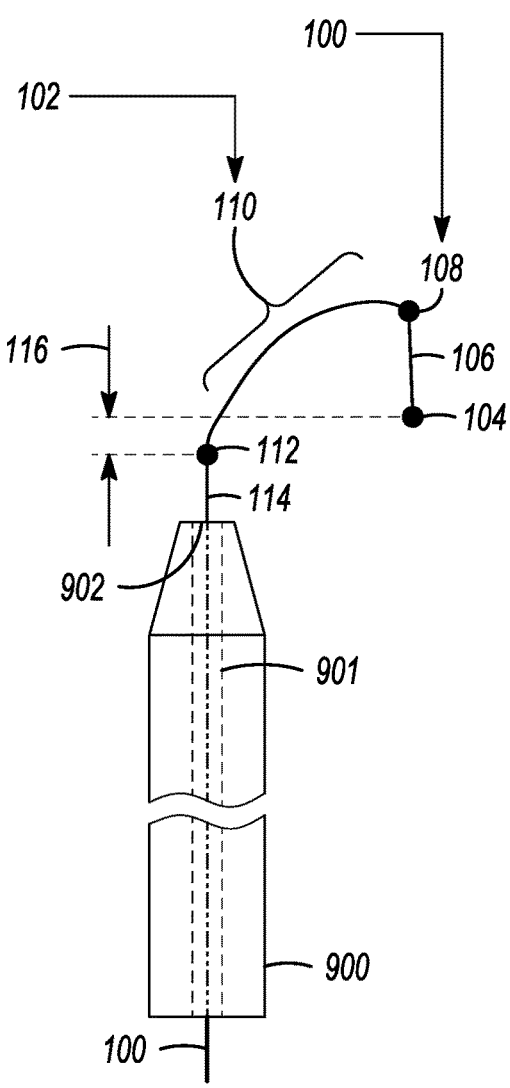

Referring to the embodiment as depicted in FIG. 6, the distal end section of the elongated guidewire assembly 100 is depicted in (exists in) a natural unstressed condition; the elongated guidewire assembly 100 is not inserted (yet) into the interior of the ancillary assembly 900 (as depicted in FIG. 10). The natural unstressed condition of the elongated guidewire assembly 100 forms once the distal end section of the elongated guidewire assembly 100 is deployed from the ancillary assembly 900. The material of the elongated guidewire assembly 100 is configured to permit flexible formation of the elongated guidewire assembly 100 between the embodiments of FIG. 6 and FIG. 10. The guidewire assembly 100 includes (preferably) super-elastic nitinol. Nitinol alloys exhibit two closely related and unique properties: shape memory effect (SME) and super-elasticity (SE; also called pseudo-elasticity or PE). Shape memory is the ability of nitinol to undergo deformation at one temperature, then recover its original, undeformed shape upon heating above its transformation temperature. Super-elasticity occurs at a narrow temperature range just above its transformation temperature; in this case, no heating is necessary to cause the undeformed shape to recover, and the material exhibits enormous elasticity, from about ten (10) to about thirty (30) times that of ordinary metal.

Figure 7:
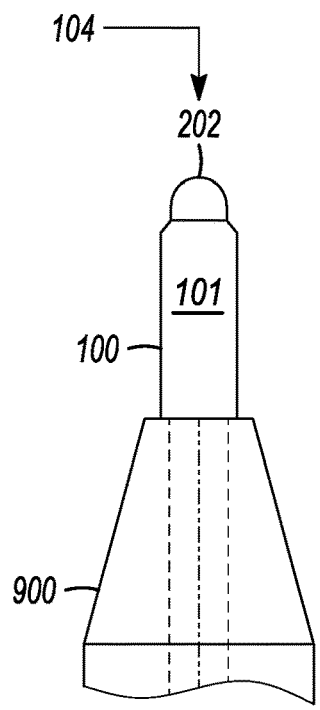

Referring to the embodiment as depicted in FIG. 7, the elongated guidewire assembly 100 includes (preferably) a puncture tip 504 having an energy emitter device, radio frequency puncture device, etc., and any equivalent thereof, such as the BAYLIS (TRADEMARK) POWERWIRE (REGISTERED TRADEMARK) radio frequency guidewire manufactured by BAYLIS MEDICAL COMPANY (headquartered in Canada). In accordance with another embodiment, the puncture tip 504 includes (and is not limited to) a mechanical cutting portion or cutting edge configured to form a puncture site (on or through tissue) by physically moving (deploying) the mechanical cutting portion into tissue.

Figure 8:
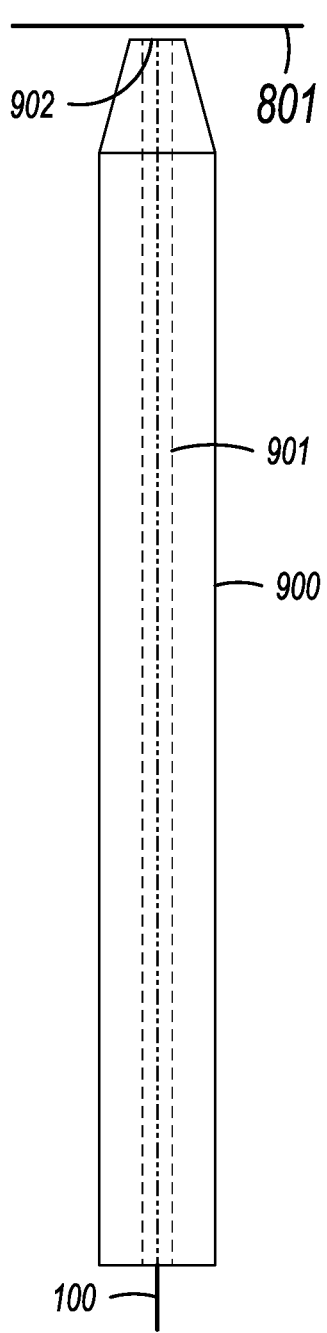

Referring to the embodiment as depicted in FIG. 8, the elongated guidewire assembly 100 is received into the interior of the ancillary assembly 900. The ancillary assembly 900 is positioned to abut the biological wall 804. The definition of "abut" includes contact, closely positioned to, adjacently positioned to, etc., and/or any equivalent thereof.

Figure 9:
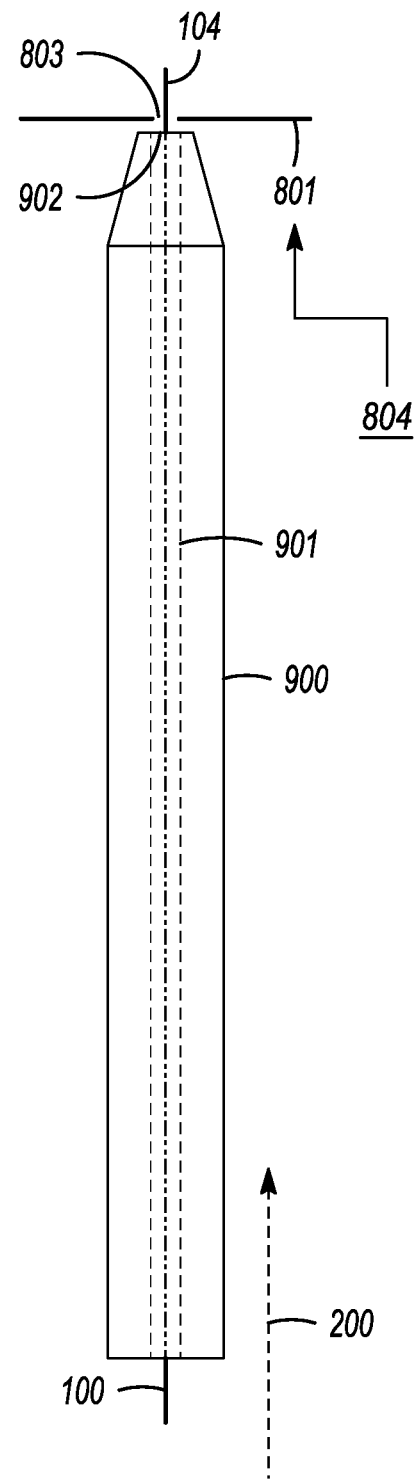

Referring to the embodiment as depicted in FIG. 9, the elongated guidewire assembly 100 is initially deployed from the interior of the ancillary assembly 900, so that the distal puncture tip 104 is extended to form the puncture hole 803 that extends through the biological wall 804. The front distal section of the elongated guidewire assembly 100 is partially deployed from the interior of the ancillary assembly 900 as depicted in FIG. 8.

Referring to the embodiment as depicted in FIG. 10, the elongated guidewire assembly 100 is further deployed from the interior of the ancillary assembly 900; this is done in such a way that the deployed distal-shaped section 102 (of the intermediate portion 110) becomes fully formed (has a fully formed shape, fully deployed shape, relaxed shape, etc. and/or any equivalent thereof).

Figure 11:
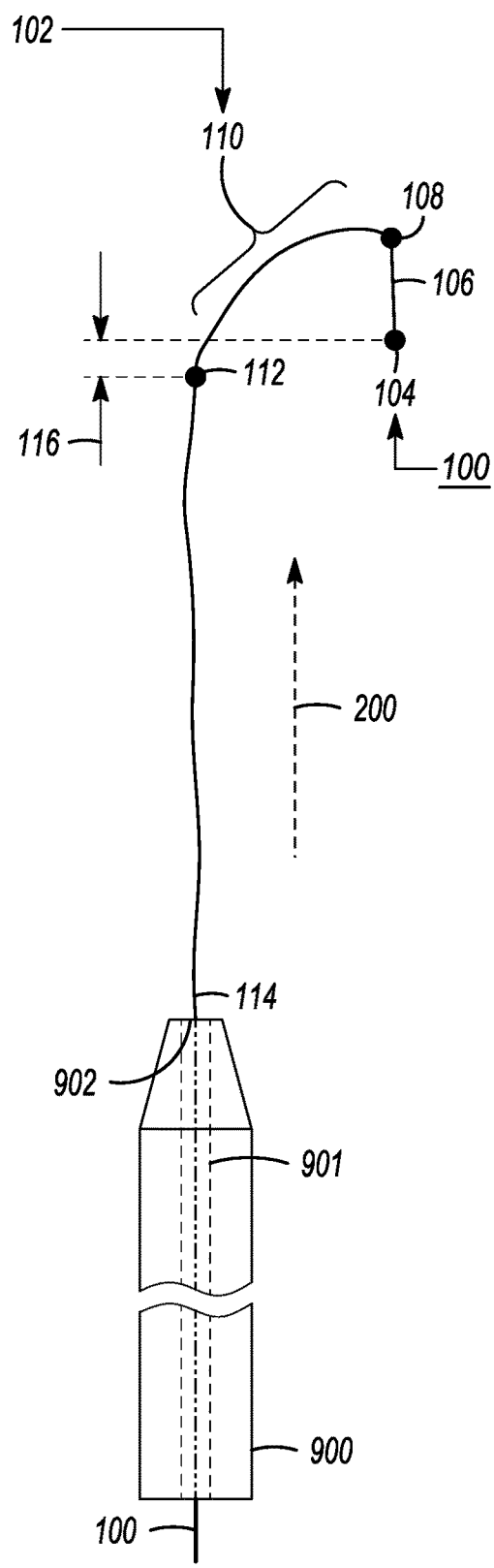

Referring to the embodiment as depicted in FIG. 11, the elongated guidewire assembly 100 is further deployed from the interior (the lumen 901) of the ancillary assembly 900. The intermediate portion 110 maintains (continues to maintain) its fully formed shape (fully shaped, fully deployed shape, etc.) while the deployed distal-shaped section 102 (or the intermediate portion 110) is translated (moved, linearly moved) further away from the tip portion (the exit portal 902) of the ancillary assembly 900.

Figure 12:
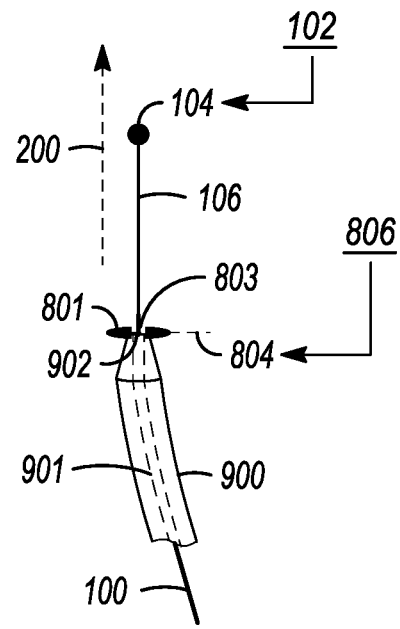
FIG. 12 to FIG. 17 depict side views of embodiments of the elongated guidewire assembly of FIG. 6.

Referring to the embodiment as depicted in FIG. 12, the ancillary assembly 900 is positioned to abut (contact, and/or any equivalent thereof) the biological wall 804. The guidewire assembly 100 is initially deployed from the interior of the ancillary assembly 900 to form the puncture hole 803 extending through the biological wall 804. The guidewire assembly 100 is partially deployed from the interior of the ancillary assembly 900 as depicted in FIG. 12.

Figure 13:
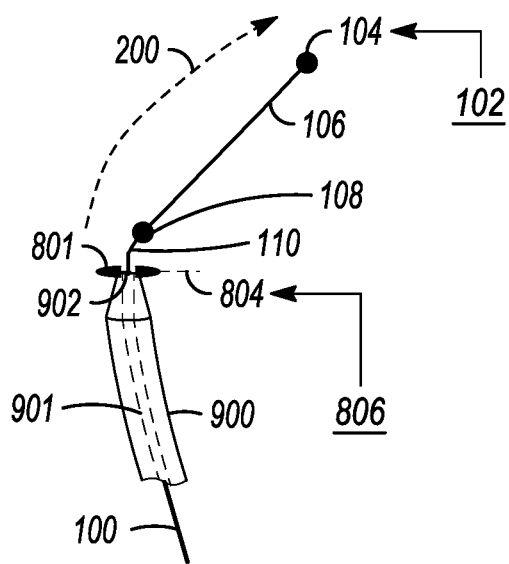

Referring to the embodiment as depicted in FIG. 13, the elongated guidewire assembly 100 is further deployed from the interior of the ancillary assembly 900. The deployed distal-shaped section 102 (or the intermediate portion 110) becomes partially formed once released, at least in part, from the interior of the ancillary assembly 900.

Figure 14:
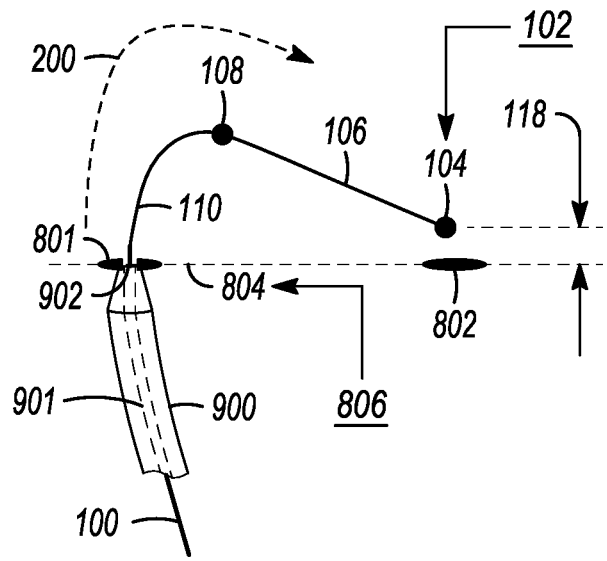

Referring to the embodiment as depicted in FIG. 14, the elongated guidewire assembly 100 is further deployed from the interior of the ancillary assembly 900. The deployed distal-shaped section 102 (or the intermediate portion 110) continues to become further formed. (but is not yet fully shaped or fully deployed).

Figure 15:
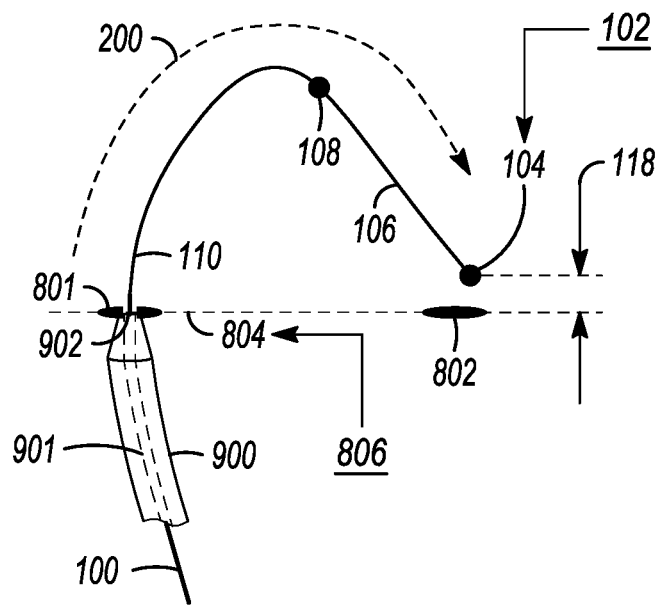

Referring to the embodiment as depicted in FIG. 15, the elongated guidewire assembly 100 is further deployed from the interior of the ancillary assembly 900. The deployed distal-shaped section 102 (or the intermediate portion 110) continues to become even further formed (but is not yet fully shaped or fully deployed).

Figure 16:
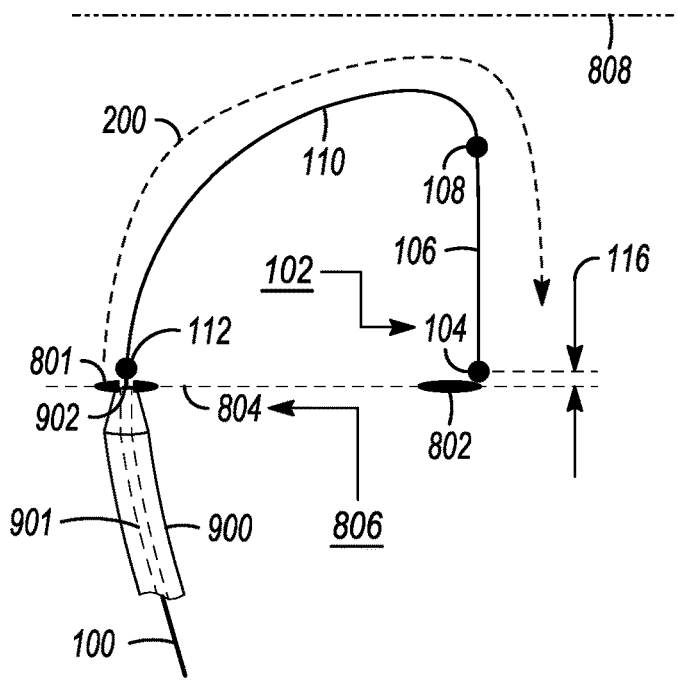

Referring to the embodiment as depicted in FIG. 16, the elongated guidewire assembly 100 is further deployed from the interior of the ancillary assembly 900; this is done in such a way that the deployed distal-shaped section 102 (or the intermediate portion 110) becomes fully formed (that is, has a fully formed shaped or fully deployed shape). The guidewire assembly 100 is configured to be deployed from the ancillary assembly 900. The guidewire assembly 100 has the distal puncture tip 104 extending from the deployed distal-shaped section 102 configured to mitigate (preferably prevent) the piercing tip from touching back on the biological wall 804 after the elongated guidewire assembly 100 is deployed from the ancillary assembly 900, and the distal puncture tip 104 crosses a biological wall 804. In this manner, inadvertent trauma (a potential for trauma) is not inflicted to the biological wall 804. The deployed distal-shaped section 102 includes (preferably) a curved shape after the elongated guidewire assembly 100 is deployed (fully deployed, as depicted in FIG. 16). The deployed distal-shaped section 102 is a relaxed shape of the distal end section of the guidewire assembly 100 once the (flexible) distal end section of the elongated guidewire assembly 100 is removed from the interior of the ancillary assembly 900.

Figure 17:
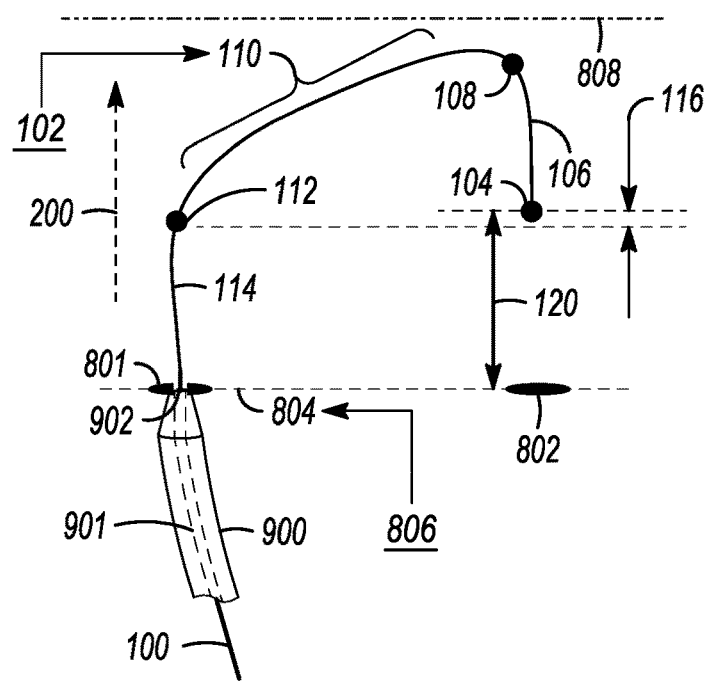

Referring to the embodiments as depicted in FIG. 16 and FIG. 17, the deployed distal-shaped section 102 includes (preferably) the distal puncture tip 104, the first linear portion 106, the first inflection portion 108, the intermediate portion 110, the second inflection portion 112 and the second linear portion 114. The first linear portion 106 (also called a straight portion) extends from the distal puncture tip 104. A first inflection portion 108 connects the first linear portion 106 to the intermediate portion 110. The first inflection portion 108 is a portion at which a change in the direction of curvature occurs for the elongated guidewire assembly 100. The intermediate portion 110 is (preferably) a curved portion or section. It will be appreciated that the intermediate portion 110 may be a linear portion (not curved, if desired). The second inflection portion 112 connects the intermediate portion 110 to the second linear portion 114. The second inflection portion 112 is a portion of the intermediate portion 110 at which a change in the direction of curvature occurs for the intermediate portion 110. Once the deployed distal-shaped section 102 is fully formed, the relative offset 116 is set up between the first inflection portion 108 and second inflection portion 112 (as depicted in FIG. 16); this is done in such a way that the distal puncture tip 104 is prevented from contacting the second tissue portion 802 (thereby preventing unwanted damage to the second tissue portion 802). As the elongated guidewire assembly 100 is further extended from the ancillary assembly 900 (as depicted in FIG. 17), the relative offset 116 is (preferably) maintained (as depicted in FIG. 17, the relative offset 116 is spaced apart from the second tissue portion 802 by an inflection portion-to-wall distance 120).

Referring to the embodiment as depicted in FIG. 17, the elongated guidewire assembly 100 is further deployed from the interior of the ancillary assembly 900, and the intermediate portion 110 is configured to maintain a fully formed shape (fully shaped or fully deployed) while the intermediate portion 110 is translated (moved, linearly moved) further away from the tip of the ancillary assembly 900.

Referring to the embodiments as depicted in FIG. 6, FIG. 10 and FIG. 11, the elongated guidewire assembly 100 includes (preferably) the deployed distal-shaped section 102. The deployed distal-shaped section 102 is configured to mitigate the piercing tip (the distal puncture tip 104) from touching back (a touch back condition) on the biological wall 804 (such as the septum of the heart) after the distal puncture tip 104 crosses the biological wall 804 (such as for cases where there is not a sufficient amount of tenting on the biological wall 804 by the ancillary assembly 900, etc.). Further, the overall outer diameter of the elongated guidewire assembly 100 (over the deployed distal-shaped section 102) closely corresponds (preferably) with the inner diameter (the lumen 901) of the ancillary assembly 900 (that the elongated guidewire assembly 100 is being deployed therefrom).

This arrangement controls the deployment of the elongated guidewire assembly 100, ensuring that the elongated guidewire assembly 100 is not able to move significantly within the bounds of the lumen 901 of the ancillary assembly 900 (such as the inner diameter of a dilator, etc.), and this condition may cause an electrode (if implemented as part of the distal puncture tip 104) to touch back on the biological wall 804 (such as the septum of the heart, etc.).

Referring to the embodiment as depicted in FIG. 6, the elongated guidewire assembly 100 is configured to be inserted into a confined space defined by a living body (the patient). The guidewire assembly 100 may include a flexible tube made from a medical grade material. The flexible tube is configured to be inserted through a narrow opening into a body cavity space (the confined space defined by the patient). The guidewire assembly 100 is (preferably) impermeable by a bodily fluid located in the confined space defined by the patient. The guidewire assembly 100 is configured (preferably) to have a wire distal portion, or to form a dual-radius shaped curve (such as, the intermediate portion 110).

Referring to the embodiment as depicted in FIG. 6, the elongated guidewire assembly 100 includes (in accordance with a preferred embodiment) bio-compatible material properties suitable for sufficient performance (such as dielectric strength, thermal performance, insulation and corrosion, water and heat resistance), such as for safe performance, for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 6, the elongated guidewire assembly 100 may include SAE (Society of Automotive Engineering) Type 304 Stainless Steel, SAE Type 304 stainless steel contains both chromium (from between about 15% to about 20%) and nickel (from between about 2% to about 10.5%) metals as the main non-iron constituents.

Referring to the embodiment as depicted in FIG. 6, the elongated guidewire assembly 100 may include a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus being applied to the shape-memory material. This is known as the shape memory effect (SME). Superelasticity (in alloys) may be observed once the shape-memory material is deformed under the presence (an application) of a stimulus force.

Referring to the embodiments as depicted in FIG. 6, the elongated guidewire assembly 100 includes (preferably) nitinol and/or stainless steel. The overall length is about 180 to about 230 centimeters (cm). The overall length of the elongated guidewire assembly 100 is not critical to the arrangement (functioning) of the intermediate portion 110. The length of the elongated guidewire assembly 100 may be any length, provided the elongated guidewire assembly 100 may be tracked through the desired anatomy (of the patient), and reach the tissue (target tissue) that the user (of the elongated guidewire assembly 100) is attempting to target for a given procedure.

Referring to the embodiments as depicted in FIG. 6, the distal puncture tip 104 is configured to puncture through tissue by any suitable means. For instance, the distal puncture tip 104 may include a mechanical puncture where the distal puncture tip 104 presents a sharp edge configured to pierce through the tissue via application of a mechanical force, etc.

Referring to the embodiments as depicted in FIG. 6, a straight section of the distal curve is offset relative to the body of the elongated guidewire assembly 100. Known (traditional) J-wires have a closed curve where the straight section is parallel with the main guidewire body. By opening up the curve, the straight section is no longer parallel with the main guidewire body and as long as the distal tip of the straight section falls on the horizontal axis of the distal curve, the straight section may not touch back on the tissue wall when being deployed (such as in the left atrium of the heart). The downside of the straight section of the distal curve, however, is that this arrangement may increase the overall footprint of the distal guidewire section, and create a snag point when the elongated guidewire assembly 100 is being tracked through the vasculature (through the body of the patient). The straight section may also be positioned at an angle relative to the main guidewire body, having a similar shape to the distal end of a hockey stick. Similar to the above concept, while this arrangement may mitigate the distal tip touching back on the wall of tissue (as depicted in FIG. 16) while the elongated guidewire assembly 100 crosses through the biological wall 804, this arrangement might potentially act as a snag point when it is being tracked through the vasculature.

Referring to the embodiment as depicted in FIG. 6, the elongated guidewire assembly 100 may be made that has a pull-wire along the length of its body and is controlled at the proximal end. When relaxed, the intermediate portion 110 (preferably having a distal curve, etc.) may be in an atraumatic shape, but when pulled taut, the elongated guidewire assembly 100 may be straightened out and/or may possess a configuration that does not allow the distal puncture tip 104 to touch back on the second tissue portion 802 after the elongated guidewire assembly 100 crosses (punctures) the first tissue portion 801 (as depicted in FIG. 16). This arrangement might allow the user to control the configuration of the shape of the intermediate portion 110 and ensure (at least in part) that the distal puncture tip 104 remains clear of the biological wall 804 (such as the septal wall of the heart) before relaxing the curve shape again and mitigating any contact.

Referring to the embodiments as depicted in FIG. 7, the distal puncture tip 104 includes the energy-emitting device 202. The energy-emitting device 202 is configured (preferably) to selectively emit radio frequency energy. The guidewire assembly 100 includes (preferably) an electrical-insulation layer 101 (that does not cover the energy-emitting device 202). The electrical-insulation layer 101 may include polytetrafluoroethylene (PTFE), a heat shrink material, etc., and any equivalent thereof. Electrical insulation may be necessary for the case where electrical current may flow through the elongated guidewire assembly 100 in order to function as desired. It will be appreciated that any suitable material that electrically insulates the electrical signals passed through an electrically conductive core (known and not depicted) of the elongated guidewire assembly 100 may be utilized. For the case where the elongated guidewire assembly 100 does not use electrical energy, the electrical insulation is not required.

Referring to the embodiment as depicted in FIG. 7, the intermediate portion 110 (the curved-shape configuration) is constrained where the energy-emitting device 202 (such as an electrode element, etc., and any equivalent thereof) positioned at a distal straight section (such as the first linear portion 106 or straight portion) cannot be positioned or located on the same horizontal plane as the main body of the elongated guidewire assembly 100.

The outer dimension of the elongated guidewire assembly 100 at the intermediate portion 110 is also close in size (approximately no less than about a 0.002 inch difference) to the inner dimension of the lumen 901 of the ancillary assembly 900 (also called an accessory device) from which the elongated guidewire assembly 100 may be deployed therefrom.

Referring to the embodiments as depicted in FIG. 7, the distal puncture tip 104 includes (preferably) a radio frequency guidewire, with an active electrode acting as the piercing distal tip. The distal curve has a dual radius fishhook configuration. The piercing distal tip terminates before the main wire body on the horizontal axis, and the curved outer diameter is no less than about 0.002 inches smaller than the inner diameter of the accessory device from which the elongated guidewire assembly 100 is being deployed therefrom.

Referring to the embodiment as depicted in FIG. 7, together with the intermediate portion 110, this arrangement is configured to control the deployment of the elongated guidewire assembly 100 and/or to mitigate (at least in part) contact (touch) between the distal puncture tip 104 and the biological wall 804 (such as, the septum) at the second tissue portion 802 after the elongated guidewire assembly 100 initially crosses (punctures) the biological wall 804 (at the first tissue portion 801).

Referring to the embodiments as depicted in FIG. 6, FIG. 7, FIG. 10 and FIG. 11, the nominal outer diameter of the main body of the elongated guidewire assembly 100 is about 0.032 inches to about 0.035 inches. The main outer diameter of the elongated guidewire assembly 100 is configured (preferably) to facilitate accessory-device exchange. The larger the outer diameter, the stiffer the elongated guidewire assembly 100, and the greater support the elongated guidewire assembly 100 may provide for tracking accessory devices along the exchange rail the elongated guidewire assembly 100 may present. The identified outer diameters of the elongated guidewire assembly 100 may be typical sizes used in a transseptal catheterization procedure, and this has no bearing on the function of the intermediate portion 110. The outer diameter may be any suitable size, provided the material remains relatively flexible to allow for the elongated guidewire assembly 100 to conform to the lumen 901 (inner lumen) of the ancillary assembly 900 (accessory device) once the elongated guidewire assembly 100 is placed inside and returned to the relaxed shape (that is, the intermediate portion 110) once the elongated guidewire assembly 100 is removed from the interior of the ancillary assembly 900 (as depicted in FIG. 10 and FIG. 11).

Referring to the embodiments as depicted in FIG. 6, FIG. 7, FIG. 10 and FIG. 11, the outer diameter of the distal curved section of the elongated guidewire assembly 100 is about 0.032 inches to about 0.035 inches (preferably, the outer diameter matches the inner diameter of the ancillary assembly 900. The curved diameter of the intermediate portion 110 is about nine (9) millimeters (mm). The length of the first linear portion 106 is about six (6) millimeters (mm). An outer diameter between about 0.032 inches and about 0.035 inches may conveniently match conventional (known) accessory devices for transseptal catheterization procedures. The outer diameter of the deployed distal-shaped section 102 does not need to conform to these specific sizes. The deployed distal-shaped section 102 may be constrained by the inner diameter (the lumen 901) of the ancillary assembly 900 that the elongated guidewire assembly 100 is deployed from (preferably, when crossing the biological wall 804, such as the interatrial septum of the heart). The outer diameter of the intermediate portion 110 may closely match (within about 0.002 inches) the inner diameter (the lumen 901) of the ancillary assembly 900 that the elongated guidewire assembly 100 is deployed out of, as this arrangement controls the way the elongated guidewire assembly 100 is deployed into the left atrium and prevents any play of the elongated guidewire assembly 100 within the lumen 901 of the ancillary assembly 900. The controlled deployment of the elongated guidewire assembly 100 is configured to mitigate (preferably prevent) secondary tissue-wall contact in concert with the distal curve geometry of the deployed distal-shaped section 102 or the intermediate portion 110 (as depicted in FIG. 16).

Referring to the embodiments as depicted in FIG. 6 and FIG. 16, the arc radii ratio (of the arcs at the first inflection portion 108 and the second inflection portion 112 bounding the intermediate portion 110) is about a radius ratio of five to one (5 to 1). This size ratio may be appropriate for a specific ideal configuration of the elongated guidewire assembly 100. It will be appreciated that the ratio may be varied if desired. Preferably, the intermediate portion 110 (the distal curve) of the elongated guidewire assembly 100 possesses two distinct radii. The first radius is larger than the second radius, which may mitigate contact (second or subsequent contact) of the distal puncture tip 104 with the biological wall 804 (after formation of the initial puncture hole by the distal puncture tip 104 after (following) initial deployment of the distal puncture tip 104 from the ancillary assembly 900, as depicted in FIG. 16). In summary, the arc radii ratio of respective arcs (at the first inflection portion and the second inflection portion) bounding the intermediate portion is about a radius ratio of five to one.

Referring to the embodiments as depicted in FIG. 6 and FIG. 7, the elongated guidewire assembly 100 includes (preferably) nitinol and/or stainless steel. Nitinol and stainless steel for the elongated guidewire assembly 100 may be used in a transseptal catheterization procedure. However, the elongated guidewire assembly 100 may include any suitable material for the task or procedure to be performed. The material of the elongated guidewire assembly 100 is configured to resiliently deform once the elongated guidewire assembly 100 is positioned or placed (at least in part) inside the interior (a hollow rigid tube or lumen) of the ancillary assembly 900 (as depicted in FIG. 8). The material of the elongated guidewire assembly 100 is also configured to elastically regain the distal curved shape (as depicted in FIG. 10 or FIG. 11) when the elongated guidewire assembly 100 is deployed outside of the ancillary assembly 900. Any material may accomplish this arrangement of the elongated guidewire assembly 100.

Figure 5:
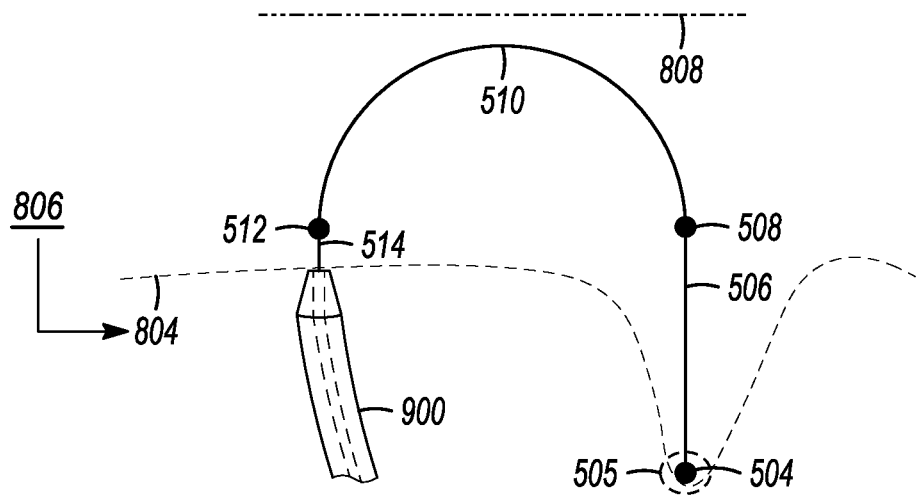
FIG. 5 depicts side view of a known guidewire assembly where the puncture tip includes an energy emitting device.

Referring to the embodiments as depicted in FIG. 6, the first linear portion 106 (also called a straight section) has a length of (preferably) about six (6) millimeters (mm) The straight section (at the distal curve) of the elongated guidewire assembly 100 facilitates (preferably) formation of a puncture through the biological wall 804 (interatrial septum, etc.). The first linear portion 106 is configured to allow a user to tent the tissue, creating a localized deformation in the tissue (as depicted in FIG. 5) which assists in pinpointing the location of crossing into the left atrium, etc. Longer straight sections may facilitate greater amounts of tenting before the elongated guidewire assembly 100 prolapses on the tissue and cannot effectively cross. The straight section can be any suitable length, however, the distal tip of the straight section (distal tip of the elongated guidewire assembly 100) cannot extend beyond the arc of the distal curve. That is, when visualizing the elongated guidewire assembly 100 on a flat plane, an imaginary horizontal line drawn from the distal tip of the elongated guidewire assembly 100 cannot touch any point on the main body of the elongated guidewire assembly 100 and, it may only contact a point on the distal curve of the elongated guidewire assembly 100.

Referring to the embodiments as depicted in FIG. 6, FIG. 16 and FIG. 17, an option may be to substitute the intermediate portion 110 with a linear distal section (straight section). This option, however, may be perceived by users as being more traumatic to vasculature compared to the distal-shaped section 102 that distributes any contact force over a larger surface area (of the biological structure 808, as depicted in FIG. 16 or FIG. 17). Another issue with this geometry is that the piercing tip of the guidewire can traumatize other tissue once inside of the left atrium.

Referring to the embodiment as depicted in FIG. 9 and FIG. 12, the elongated guidewire assembly 100 is configured to (preferably or may be utilized for) forming a puncture (such as the puncture hole 803, as depicted in FIG. 9 and/or FIG. 12); this is done in such a way that the puncture extends through a biological wall, such as the interatrial septum (of the heart of a patient) associated with a transseptal catheterization procedure, etc.

Referring to the embodiments as depicted in FIG. 12 to FIG. 17, the elongated guidewire assembly 100 may be deployed across the septum (an example of the biological structure 808). The dual radius design may mitigate the risk of the distal puncture tip 104 touching back on the septum (as depicted in FIG. 16) if there is insufficient tenting applied by the ancillary assembly 900, etc.

Referring to the embodiments as depicted in FIG. 6, FIG. 7, FIG. 8, FIG. 9, FIG. 11 and FIG. 13 to FIG. 17, there are depicted embodiments of the apparatus for (that is, configured to be used with) the ancillary assembly 900. The ancillary assembly 900 may include a dilator assembly, a sheath assembly, etc., and/or any equivalent thereof. The ancillary assembly 900 has the exit portal 902 (as depicted in FIG. 12) configured to be positioned proximate to (to preferably abut or contact) the first tissue portion 801 (as depicted in FIG. 14), with the first tissue portion 801 spaced apart from the second tissue portion 802 (as depicted in FIG. 14) of the biological wall 804 of the patient 806. The second tissue portion 802 is spaced apart from the first tissue portion 801. The apparatus includes and is not limited to (comprises) an elongated guidewire assembly 100. For this case, the elongated guidewire assembly 100 and the ancillary assembly 900 are manufactured and/or sold separately to the end user, etc. It will be appreciated that the term "abuts" or "abut" includes contact, is positioned proximate to, is positioned adjacent to, etc., and/or any equivalent thereof.

Referring to the embodiments as depicted in FIG. 6, FIG. 7, FIG. 8, FIG. 9, FIG. 11 and FIG. 13 to FIG. 17, there are depicted embodiments of an apparatus. The apparatus includes a synergistic combination of the elongated guidewire assembly 100 and the ancillary assembly 900. For this case, the elongated guidewire assembly 100 and the ancillary assembly 900 are manufactured and/or sold together to the end user, etc.

Referring to the embodiments as depicted in FIG. 8, FIG. 9 and FIG. 12, the elongated guidewire assembly 100 has the distal puncture tip 104 configured to be received (at least in part) in the elongated lumen 901 of the ancillary assembly 900 (as depicted in FIG. 8).

While the elongated guidewire assembly 100 and the distal puncture tip 104 are received (at least in part) in (along) the elongated lumen 901, the elongated guidewire assembly 100 has a flexible shape that remains conforms to (is configured to be fit within) the diameter of the elongated lumen 901 (as depicted in FIG. 8). The distal puncture tip 104 is also configured to be deployed (at least in part) from the elongated lumen 901 of the ancillary assembly 900 (as depicted in FIG. 9 or FIG. 12). The guidewire assembly 100 is moved (maneuvered) along a deployment direction 200 from the lumen 901.

Referring to the embodiments as depicted in FIG. 8, FIG. 9 and FIG. 12, the elongated guidewire assembly 100 is configured to be deployed from the exit portal 902 of the ancillary assembly 900. The guidewire assembly 100 is moved (maneuvered) along the deployment direction 200 from the ancillary assembly 900. The exit portal 902 (of the ancillary assembly 900) is configured to abut (contact, etc.) the first tissue portion 801 of the biological wall 804 (of a patient 806, as depicted in FIG. 9 and FIG. 12). This is done (preferably) so that the distal puncture tip 104 may puncture the first tissue portion 801 once the distal puncture tip 104 is deployed from the ancillary assembly 900.

Referring to the embodiments as depicted in FIG. 6, FIG. 11 and FIG. 13 to FIG. 17, the elongated guidewire assembly 100 has the deployed distal-shaped section 102 (also called a predetermined deployed shape or a deployed instance of the distal-shaped section 102) with the distal puncture tip 104. As depicted in FIG. 16, the deployed instance of the distal-shaped section 102 is fully formed (released). The deployed distal-shaped section 102 is the hall shape of the distal section (frontal section) of the elongated guidewire assembly 100 after (once) the elongated guidewire assembly 100 is (at least in part) removed (deployed) via the exit portal 902 (as depicted in FIG. 6, FIG. 16 and/or FIG. 17). The distal puncture tip 104 is configured to extend toward, and become positioned adjacently to (and without puncturing) the second tissue portion 802 of the biological wall 804 of the patient 806 (as depicted in FIG. 16, that is once the distal-shaped section 102 becomes fully formed by becoming fully released from the ancillary assembly 900). This is done, preferably, after the deployed distal-shaped section 102 is fully formed (released) from the lumen 901 of the ancillary assembly 900 (via the exit portal 902). This is done, preferably, after (A) the exit portal 902, in use, abuts (contacts) the first tissue portion 801, and (B) the elongated guidewire assembly 100 is deployed (preferably, fully deployed, or at any time during deployment of the distal-shaped section 102) from the exit portal 902 of the ancillary assembly 900.

Referring to the embodiments as depicted in FIG. 11 to FIG. 17, the elongated guidewire assembly 100 and the distal puncture tip 104 are (preferably) configured to be deployed, at least in part, from the exit portal 902 of the ancillary assembly 900 (for instance, as depicted in FIG. 12). This is done, preferably, in such a way that the elongated guidewire assembly 100, in a deployed condition (fully deployed condition or state), forms the deployed distal-shaped section 102 (a predetermined curve), as depicted in FIG. 16. This is done (preferably) after the elongated guidewire assembly 100 is deployed (preferably, fully deployed) from the exit portal 902 (as depicted in FIG. 16).

Referring to the embodiments as depicted in FIG. 10, FIG. 11 and FIG. 13 to FIG. 17, the distal puncture tip 104 (preferably) extends from the distal portion of the deployed distal-shaped section 102 after the elongated guidewire assembly 100 is deployed from the exit portal 902 (as depicted in FIG. 10, FIG. 11 and/or FIG. 16). For instance, as depicted in FIG. 16, the elongated guidewire assembly 100 is fully deployed from the exit portal 902. The deployed distal-shaped section 102 is fully formed and set up, as depicted in FIG. 16. The deployed distal-shaped section 102 is partially formed and set up, as depicted in FIG. 12 to FIG. 15.

Referring to the embodiments as depicted in FIG. 8, FIG. 9 and FIG. 12, the distal puncture tip 104 is (preferably) also configured to puncture the first tissue portion 801 of the biological wall 804, and form a puncture hole 803 extending through the first tissue portion 801 of the biological wall 804 (as depicted in FIG. 9 or FIG. 12). The is done (preferably) after (A) the exit portal 902 is positioned proximate to (abuts or contacts) the first tissue portion 801 of the biological wall 804, and (B) the distal puncture tip 104 is deployed or continues to be deployed (at least in part along the deployment direction 200) from the exit portal 902 toward the second tissue portion 802 of the biological wall 804 (as depicted in FIG. 14, FIG. 15 and FIG. 16).

Referring to the embodiment as depicted in FIG. 16, the distal puncture tip 104 is (preferably) also configured to extend toward, and become positioned adjacently to (and without puncturing) the second tissue portion 802 of the biological wall 804 of the patient 806 (as depicted in FIG. 16). The is done (preferably) after: (A) the exit portal 902, in use, abuts (contacts) the first tissue portion 801, and (B) the distal puncture tip 104 is deployed (that is, fully deployed) from the exit portal 902, and the distal puncture tip 104, in use, forms the puncture hole 803 extending through the biological wall 804.

Referring to the embodiment as depicted in FIG. 16, the elongated guidewire assembly 100 has (preferably) the deployed distal-shaped section 102 with the distal puncture tip 104 (extended from the interior of the ancillary assembly 900). The distal puncture tip 104 is (preferably) also configured to extend toward, and be positioned proximate to (without extending beyond) the second tissue portion 802. This is done (preferably) after (A) the exit portal 902, in use, abuts the first tissue portion 801, and (B) the elongated guidewire assembly 100 is deployed from the exit portal 902.

Referring to the embodiments as depicted in FIG. 8, FIG. 9, FIG. 10, FIG. 11, FIG. 12, FIG. 16 and FIG. 17, there are depicted steps of a method of using the ancillary assembly 900 and the elongated guidewire assembly 100.

With reference to the embodiments as depicted in FIG. 8 and FIG. 9, the method includes (preferably) deploying, at least in part, the elongated guidewire assembly 100 and the distal puncture tip 104 from the exit portal 902 of the ancillary assembly 900 (as depicted in FIG. 9). This is done (preferably) in such a way that the elongated guidewire assembly 100, in a deployed condition (or partially deployed condition), forms a deployed distal-shaped section 102 (predetermined curve) after the elongated guidewire assembly 100 is deployed from the exit portal 902.

The fully formed instance of the deployed distal-shaped section 102 is depicted in FIG. 10, FIG. 11, FIG. 16 and/or FIG. 17.

With reference to the embodiments as depicted in FIG. 10 and FIG. 11, the method also includes (preferably) extending the distal puncture tip 104 from the distal portion of the deployed distal-shaped section 102. This is done (preferably) after the elongated guidewire assembly 100 is deployed (at least in part) from the exit portal 902.

With reference to the embodiments as depicted in FIG. 9 and FIG. 12, the method also includes (preferably) puncturing, with the distal puncture tip 104, the first tissue portion 801 of the biological wall 804, so that the distal puncture tip 104 forms (in use) the puncture hole 803 (extending through the first tissue portion 801 of the biological wall 804, as depicted in FIG. 9 or FIG. 12). This is done (preferably) after (A) the exit portal 902 is positioned proximate to (abuts or contacts) the first tissue portion 801 of the biological wall 804, and (B) the distal puncture tip 104 is deployed from the exit portal 902 toward the second tissue portion 802 of the biological wall 804.

With reference to the embodiments as depicted in FIG. 16 and FIG. 17, the method also includes (preferably) extending and positioning the distal puncture tip 104 toward and adjacent to (without puncturing) the second tissue portion 802 of the biological wall 804 of the patient 806 (as depicted in FIG. 16). This is done (preferably) after (A) the exit portal 902, in use, abuts (contacts) the first tissue portion 801, and (B) the distal puncture tip 104 is deployed from the exit portal 902, and the distal puncture tip 104, in use, forms the puncture hole 803 extending through the biological wall 804.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description anchor drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for an ancillary assembly having an exit portal configured to be positioned proximate to a first tissue portion and a second tissue portion of a biological wall of a patient, the apparatus comprising:
    an elongated guidewire assembly having a distal-shaped section including a distal puncture tip, a first linear portion extending from the distal puncture tip to a first inflection portion, an intermediate portion extending from the first inflection portion to a second inflection portion, a second linear portion extending from the second inflection portion towards a proximal end of the elongated guidewire, the elongated guidewire assembly configured to be received in an elongated lumen of the ancillary assembly; and
    the distal puncture tip configured to be deployed from the exit portal of the ancillary assembly in such a way that the elongated guidewire assembly, in a relaxed deployed condition, forms a deployed distal-shaped section having a distal curve and a relative offset between the first inflection portion and the second inflection portion after the elongated guidewire assembly is in the deployed condition, such that, in the deployed condition the distal puncture tip does not extend proximally beyond a plane orthogonal to a longitudinal axis of the second linear portion and passes through the second inflection point.

2. The apparatus of claim 1, wherein:
    the elongated guidewire assembly, in the deployed condition, is configured to extend toward, and be positioned proximate to, without extending beyond, the second tissue portion of the biological wall of the patient after:
    the exit portal, in use, abuts the first tissue portion; and
    the elongated guidewire assembly is in the deployed condition from the exit portal.

3. The apparatus of claim 1, wherein:
    the distal puncture tip extends from a distal portion of the deployed distal-shaped section after the elongated guidewire assembly is deployed from the exit portal.

4. The apparatus of claim 3, wherein:
    the distal puncture tip is also configured to puncture the first tissue portion of the biological wall and form a puncture hole extending through the first tissue portion of the biological wall.

5. The apparatus of claim 4, wherein:
    the distal puncture tip is also configured to extend toward, and become positioned adjacently to, without puncturing, the second tissue portion of the biological wall of the patient.

6. The apparatus of claim 5, wherein:
    the distal puncture tip is also configured to extend toward, and become positioned adjacently to, without puncturing, the second tissue portion of the biological wall of the patient after:
    the exit portal, in use, abuts the first tissue portion; and
    the distal puncture tip is deployed from the exit portal, and the distal puncture tip, in use, forms the puncture hole extending through the biological wall.

7. The apparatus of claim 3, wherein:
the distal puncture tip is also configured to puncture the first tissue portion of the biological wall and form a puncture hole extending through the first tissue portion of the biological wall after:
the exit portal is positioned proximate to the first tissue portion of the biological wall; and
the distal puncture tip is deployed from the exit portal toward the second tissue portion of the biological wall.

8. The apparatus of claim 1, wherein:
the distal puncture tip is configured to extend toward, and become positioned adjacently to, without puncturing, the second tissue portion of the biological wall of the patient after the deployed distal-shaped section is in the deployed condition.

9. The apparatus of claim 1, wherein: the intermediate portion includes the distal curve.

10. The apparatus of claim 1, wherein: an arc radii ratio, of respective arcs at the first inflection portion and the second inflection portion, bounding the intermediate portion is about a radius ratio of five to one.

11. The apparatus of claim 1, wherein the elongated guidewire assembly includes a shape-memory material.

12. The apparatus of claim 1, wherein: the distal puncture tip includes an energy-emitting device.

13. The apparatus of claim 1, wherein: the first linear portion is configured to tent the biological wall.

14. An apparatus, comprising:
an ancillary assembly having an exit portal configured to be positioned proximate to a first tissue portion and a second tissue portion of a biological wall of a patient;
an elongated guidewire assembly having a distal-shaped section including a distal puncture tip, a first linear portion extending from the distal puncture tip to a first inflection portion, an intermediate portion extending from the first inflection portion to a second inflection portion, a second linear portion extending from the second inflection portion towards a proximal end of the elongated guidewire, the elongated guidewire assembly being configured to be received in an elongated lumen of the ancillary assembly;
the distal-shaped section configured to be deployed from the exit portal of the ancillary assembly in such a way that the elongated guidewire assembly, in a relaxed deployed condition, forms a deployed distal-shaped section having a distal curve and a relative offset between the first inflection portion and the second inflection portion after the elongated guidewire assembly is in the deployed condition, such that, in the deployed condition, the distal puncture tip does not extend proximally beyond a plane orthogonal to a longitudinal axis of the second linear portion and passes through the second inflection point;
the distal puncture tip extending from a distal portion of the deployed distal-shaped section after the elongated guidewire assembly is deployed from the exit portal;
the distal puncture tip also configured to puncture the first tissue portion of the biological wall and form a puncture hole extending through the first tissue portion of the biological wall after:
the exit portal is positioned proximate to the first tissue portion of the biological wall; and
the distal puncture tip is deployed from the exit portal toward the second tissue portion of the biological wall; and
the distal puncture tip also configured to extend toward, and become positioned adjacently to, without puncturing, the second tissue portion of the biological wall of the patient after:
the exit portal, in use, abuts the first tissue portion, and
the distal puncture tip is deployed from the exit portal, and the distal puncture tip, in use, forms the puncture hole extending through the biological wall.

15. The apparatus of claim 14, wherein the distal curve possesses two distinct radii.

16. The apparatus of claim 14, wherein the intermediate portion includes the distal curve.

17. The apparatus of claim 14, wherein the first linear portion is configured to tent the biological wall.

* * * * *